(12) United States Patent
Janssen (10) Patent No.: US 12,268,788 B2
(45) Date of Patent: Apr. 8, 2025

(54) UV MODULE WITHIN CONSUMER MACHINES

(71) Applicant: PHILIPS LIGHTING HOLDING B.V., Eindhoven (NL)

(72) Inventor: Merlijn Antonius Petrus Maria Janssen, Eindhoven (NL)

(73) Assignee: SIGNIFY HOLDING, B.V., Eindhoven (NL)

( * ) Notice: Subject to any disclaimer, the term of this patent is extended or adjusted under 35 U.S.C. 154(b) by 1662 days.

(21) Appl. No.: 16/301,475

(22) PCT Filed: Feb. 2, 2017

(86) PCT No.: PCT/EP2017/052285
§ 371 (c)(1),
(2) Date: Nov. 14, 2018

(87) PCT Pub. No.: WO2017/202508
PCT Pub. Date: Nov. 30, 2017

(65) Prior Publication Data
US 2020/0009279 A1 Jan. 9, 2020

(30) Foreign Application Priority Data

May 24, 2016 (EP) ..................................... 16170973

(51) Int. Cl.
*A61L 2/00* (2006.01)
*A23L 2/50* (2006.01)
(Continued)

(52) U.S. Cl.
CPC .................... *A61L 2/10* (2013.01); *A23L 2/50* (2013.01); *A23L 3/28* (2013.01); *A61L 2/26* (2013.01); *A61L 9/20* (2013.01); *C02F 1/325* (2013.01); *A23V 2002/00* (2013.01); *A61L 2202/11* (2013.01); *A61L 2202/122* (2013.01); *A61L 2209/12* (2013.01); *A61L 2209/16* (2013.01); *C02F 2201/3222* (2013.01); *C02F 2303/04* (2013.01); *F24F 8/22* (2021.01)

(58) Field of Classification Search
CPC .... F24F 13/00; C02F 1/32; A61L 2/00; A61L 2/10; A61L 9/00; A61L 9/20; A61L 2202/20; A61L 2209/00; A61L 2202/11; A61L 2/26; A61L 2202/14; A61L 2202/122
USPC ............. 422/24; 261/30, 107; 250/453, 437; 210/748.11
See application file for complete search history.

(56) References Cited

U.S. PATENT DOCUMENTS

| 4,867,052 A | 9/1989 | Cipelletti |
| 7,842,932 B2 | 11/2010 | Knight et al. |

(Continued)

FOREIGN PATENT DOCUMENTS

| CN | 201396699 Y | 2/2010 |
| CN | 101681963 A | 3/2010 |

(Continued)

*Primary Examiner* — Monzer R Chorbaji (57) ABSTRACT

Methods and apparatus are provided for ultraviolet (UV) fluid purification, wherein the fluid is in a gaseous, liquid or solid form or combination thereof, comprising UV-C LED modules having improved light extraction efficiency. UV-C LED(s) are in optical communication with one or more UV-C transmissive window elements.

12 Claims, 4 Drawing Sheets

(51) Int. Cl.
  *A23L 3/28* (2006.01)
  *A61L 2/10* (2006.01)
  *A61L 2/26* (2006.01)
  *A61L 9/20* (2006.01)
  *B01D 17/06* (2006.01)
  *C02F 1/32* (2023.01)
  *G01N 21/00* (2006.01)
  *F24F 8/22* (2021.01)

(56) References Cited

U.S. PATENT DOCUMENTS

| | | |
|---|---|---|
| 2004/0005260 A1 | 1/2004 | Mulvaney |
| 2006/0138443 A1* | 6/2006 | Fan .................. H01L 33/56 257/100 |
| 2009/0001372 A1* | 1/2009 | Arik .................. H01L 33/486 257/58 |
| 2013/0175711 A1* | 7/2013 | Nutter .................. F24F 6/02 261/30 |
| 2014/0061706 A1 | 3/2014 | Bae et al. |
| 2014/0264070 A1 | 9/2014 | Bettles et al. |
| 2014/0367734 A1 | 12/2014 | Kneissl et al. |
| 2016/0027970 A1* | 1/2016 | Shatalov .............. H01L 33/507 438/27 |

FOREIGN PATENT DOCUMENTS

| | | |
|---|---|---|
| CN | 101929651 A | 12/2010 |
| CN | 101937962 A | 1/2011 |
| CN | 201892092 U | 7/2011 |
| CN | 102219289 A | 10/2011 |
| CN | 102983245 A | 3/2013 |
| CN | 103682047 A | 3/2014 |
| CN | 103715331 A | 4/2014 |
| CN | 204042547 U | 12/2014 |
| CN | 105304787 A | 2/2016 |
| CN | 205037251 U | 2/2016 |
| DE | 202011000504 U1 | 10/2011 |
| EP | 1872801 A2 | 1/2008 |
| JP | 2012078053 A | 4/2012 |
| JP | 2018509290 A | 4/2018 |
| KR | 20130092224 A | 8/2013 |
| KR | 20150008772 A | 1/2015 |
| RU | 142036 U1 | 6/2014 |
| WO | 0263185 A1 | 4/1988 |
| WO | WO2013085965 A1 | 6/2013 |
| WO | 2014058011 A1 | 4/2014 |
| WO | 2016000980 A1 | 1/2016 |
| WO | 2016014762 A1 | 1/2016 |
| WO | WO2016008799 A1 | 1/2016 |
| WO | 2016073831 A1 | 5/2016 |
| WO | WO2016150718 A1 | 9/2016 |

\* cited by examiner

UV MODULE WITHIN CONSUMER MACHINES

CROSS-REFERENCE TO PRIOR APPLICATIONS

This application is the U.S. National Phase application under 35 U.S.C. § 371 of International Application No. PCT/EP2017/052285, filed on Feb. 2, 2017, which claims the benefit of European Patent Application No. 16170973.8, filed on May 24, 2016. These applications are hereby incorporated by reference herein.

FIELD OF THE INVENTION

This invention relates to the use of an ultraviolet light emitting module within consumer devices.

BACKGROUND OF THE INVENTION

The use of UV light—in particular UV-C light—for the purification of fluids, or more precisely the disinfection and sterilization of fluids, (hereafter referred, for the sake of simplicity, as fluid purification or purification of fluid) is a well-known and well established technical practice. Utilizing UV-C is an efficient way for purifying fluid reservoirs without the need to add chemicals or for frequent cleaning. UV-C light at sufficiently short wavelengths is mutagenic to bacteria, viruses and other microorganisms. At a wavelength of around 265 nm, UV breaks molecular bonds of DNA in the cells of microorganisms, producing thymine dimers in the DNA, thereby destroying the DNA structure necessary to reproduce the cell, rendering them harmless or prohibiting growth and reproduction. The main considerations when designing a UV-C system for UV-C inactivation to be efficient are source intensity and exposure time. Source intensity (also known as lamp intensity) is a function of the sources' radiant energy and the distance to the surface to be irradiated. Once an intensity factor is established it is simple to determine how long the surface needs to be exposed.

More recently, demand has grown for UV-C fluid purification devices which can utilize technologies from the fast developing field of UV-C LED light sources. It is well known, for example, that semiconductor materials of group IIIA-nitrides ($Al_xGa_{1-x-y}In_yN$, [$0<\!/\!=x+y<\!/\!=1$]) have direct band gaps that can be used to generate electromagnetic radiation in the wavelength of ultraviolet (UV). For instance, ($Al_xGa_{1-x}N$ ($0<x<1$)) is often utilized as the component for light emitting diode (LED), generating UV radiation below 365 nm.

In terms of above mentioned fluid purification, UV-C LED solutions confer numerous advantages over more traditional fluorescent or incandescent UV-C lamps, including for example fast switching capability, small form factor, long lifetime, and a significantly 'cleaner' material composition—comprising few hazardous or harmful component materials.

Desired therefore is a UV-C LED fluid purification device, comprising UV-C LED packages having an improved light extraction efficiency, thereby allowing for an increased light intensity capacity, without incurring any increased bulk or weight to the device, nor significantly increasing overall operating costs.

SUMMARY OF THE INVENTION

The invention is defined by the claims.

According to an aspect of the invention, there is provided a UV-C purification device, comprising:
  one or more UV-C LED modules for administering UV-C light to fluid in a gaseous, liquid, or solid form or a combination thereof, each module comprising:
  one or more UV-C LED, and
  one or more UV-C-transmissive window elements,
  wherein the one or more UV-C LED is in optical communication with the one or more UV-C-transmissive window elements.

According to a second aspect of the invention, there is provided a fluid purification method, comprising:
  administering UV-C light to fluid in a gaseous, liquid, or solid form or a combination thereof, the UV-C light being generated by one or more UV-C LED modules, each module comprising:
  one or more UV-C LED, and
  one or more UV-C-transmissive window elements,
  wherein the one or more UV-C LED is in optical communication with the one or more UV-C-transmissive window elements.

There are thus provided UV-C purification devices comprising UV-C LED modules for the application of UV-C light to fluid in a gaseous, liquid or solid form or a combination thereof, each module comprising one, or a plurality of, UV-C LED(s) and one, or a plurality of UV-C-transmissive window element(s) for transmitting the light generated by the LED. The UV-C-transmissive window element(s) may be translucent, transparent or even opaque to light having visible wavelengths. The UV-C transmissive window element may comprise, for example, silicone, poly crystalline aluminium oxide (PCA), UVC transparent glass, quartz, synthetic quartz ($SiO_2$), fluorinated ethylene propylene (FEP).

In some embodiments, modules may be located or integrated into consumer devices such as, for example, a coffee machine, a room humidifier, the cool drinks dispenser on the front of the fridge. The UV-C LED may be arranged to administer UV-C light to a fluid in liquid form within the coffee machine, this may be to internal pipework through which fluid flows or it may be arranged to administer UV-C light to a reservoir containing a fluid (in this case water) within the machine. The UV-C LED may be arranged to administer UV-C light to a fluid in solid form within an ice reservoir located in a device, for instance a fridge freezer. Preferably the ice reservoir or ice bucket has a cover. It was surprisingly found that the UV-C LED can be placed anywhere to administer UV-C light to a fluid in solid form (i.e., ice), rather than having to be below the level of the water in fluid form as is nearly always the case for efficient water purification due to the reflection at the air-water interface when the UV-LED is located above the water level. Further, the UVC LED may be arranged to administer UV-C light to a fluid in liquid form within the cool drinks dispenser integrated into the fridge freezer. Further, the UV-C LED may be arranged to administer UV-C light to fluid in both a liquid and an solid form at the same time, this may prove advantageous in situations where a mixture of pellets of ice are mixed into a liquid to form a slush. The liquid may be an uncarbonated juice or other liquid such as coffee. The machines to create such slush drinks generally have a stirrer or auger that rotates at a constant speed to mix sugar and the water molecules so that they bond before the water freezes. The result is a soft, wet slurry mixture.

In some embodiments, modules may be located or integrated into industrial devices such as, for example, ice machines such as in a restaurant, hotel, public space or fast food outlet. In some embodiments, modules may be located or integrated in an ice storage bin such as in a restaurant, supermarket, fast food outlet, food preparation area, fish market, or cannery.

Embodiments of the invention may be arranged to administer UV-C light to a colloid. Examples of such suspensions are whipped cream, paint, blood and water mist.

Colloids are a uniform dispersion of fine particles in a medium. The fine particles have a diameter of between 1 and 1000 nm and may be solid, liquid or a gas. The medium that they are suspended in may be a solid, liquid or a gas (however, gas colloids cannot be suspended in a gas).

Legionnaires disease is spread chiefly by breathing in mist that contains the *Legionella* bacteria. The bacteria is found naturally in fresh water and can contaminate hot water tanks, hot tubs, air conditioning systems (HVAC), ponds, fountains etc. It can also be spread when the water containing the bacteria becomes aspirated via suction. It is estimated that legionnaires disease is the cause of approximately 2-9% of worldwide pneumonia cases.

The primary concern is when water containing the bacteria is aerosolized, i.e. when the droplet sizes of the water become small enough to be carried into the air. An atomizer is a very effective way of disinfecting a room when the correct disinfectants (mixed with a water source) are aerosolized or very effective at extinguishing a fire. Unfortunately they are also a very effective way of spreading the *Legionella* bacteria if the water source for the fire suppression system or the disinfectant is contaminated with the bacteria. This can pose a serious health risk.

*Legionella* bacteria, especially *Legionella* pneumonia (the cause of over 90% of legionnaires disease cases), thrives in aquatic systems where it is established within amoebae in a symbiotic relationship. In the built environment, central air conditioning systems in office buildings, hotels, and hospitals are sources of contaminated water. Other places it can dwell include cooling towers used in industrial cooling systems, evaporative coolers, nebulizers, humidifiers, whirlpool spas, hot water systems, showers, windshield washers, fountains, room-air humidifiers, ice-making machines, and misting systems typically found in grocery-store produce sections.

The disease may also be transmitted from contaminated aerosols generated in hot tubs if the disinfection and maintenance program is not followed rigorously. Freshwater ponds, creeks, and ornamental fountains are potential sources of *Legionella*. The disease is particularly associated with hotels, fountains, cruise ships, and hospitals with complex potable water systems and cooling systems. Respiratory care devices such as humidifiers and nebulizers used with contaminated tap water may contain *Legionella* species, so using sterile water is very important.

Reduction of the risk of spreading legionnaires disease is currently achieved by a number of methods;
  Keeping the water temperature in the system below 20° C. or above 50° C.,
  Preventing stagnation by removing any pipework that has no outlets, if prevention is not possible then thorough disinfection must occur before use,
  Preventing the formation of biofilms, this can be achieved by replacing construction materials that promote the growth of the biofilm, or by reducing the quantity of nutrients for bacterial growth entering the system,
  Periodic disinfection of the system by using high heat or a chemical biocide or chlorination where appropriate,
  Intelligent system design that reduces the production of aerosols and reducing the human exposure to them.

It can be seen that such methods are energy intensive in the case of continual maintenance of the water temperature or chemically intensive. The use of a UV-C purification device near to the outlet of the system may help to reduce the risks of spreading the disease. Due to the small form factor of UV-C LEDs it is also possible to place them in shower heads or within taps to purify the fluid prior to use. The principle source of hospital-acquired *Legionella* pneumonia is the drinking water distribution system and currently has a mortality rate of over 25%.

Embodiments of the invention may be arranged to administer UV-C light to an emulsion. An emulsion is a type of colloid system and is a uniform dispersion of one liquid in another liquid which are immiscible. Although the terms colloid and emulsion are sometimes used interchangeably, emulsion should be used when both phases, dispersed and continuous, are liquids. An example of such an emulsion is oil and water which when shaken together form a cloudy suspension. If left to rest, the oil and water will separate. Further examples are butter, margarine, hand cream, mayonnaise and ice cream.

Ice cream is a combination of air, ice crystals, fat globules, and a liquid syrup. These are combined to make a colloidal system. (Also called colloidal dispersion, colloidal suspension.) An intimate mixture of two substances, one of which, called the dispersed phase (or colloid), is uniformly distributed in a finely divided state through the second substance, called the dispersion medium (or dispersing medium). During freezing, most of the water is frozen into ice. Small ice crystals are needed for smooth ice cream. Beating and aeration are carried out simultaneously with the freezing so as to form small air bubbles. These small bubbles are stabilized by de-emulsified fat. Air makes up between 30-50% of an ice cream's final volume. The ice cream may be dispensed using a point of use solution such as a soft-ice machine. The nozzles of these machines require frequent cleaning and sterilization to prevent contamination. If a period of time occurs between the dispensing of an ice cream and the next dispensation it is plausible that microorganisms may begin to multiply and thus the next ice-cream may contain these microorganisms. Therefore embodiments of the invention may be arranged to administer UV-C light to the ice cream proximate to the outlet of the nozzle. The UV-C purification device may be arranged next to a pipe or passage through which the fluid to be purified passes, for example, through which ice cream passes between the area of the machine in which the ice cream is mixed and the dispensing nozzle. The passage may pass through the UV-C purification device or the UV-C device may be located proximate to the passage and arranged to irradiate the fluid passing through the passage. Microorganisms are an organism that is too small to be seen by the unaided human eye and include bacteria, fungi, archaea or protists and viruses.

Embodiments of the invention may be arranged to administer UV-C light to a suspension. A suspension is a heterogeneous mixture containing solid particles that are sufficiently large for sedimentation. Usually they must be larger than one micrometer. It is when particles are left floating around freely in a solvent. The internal phase (solid) is dispersed throughout the external phase (fluid) through mechanical agitation, with the use of certain excipients or suspending agents, unlike colloids a suspension will settle over time if left undisturbed.

Embodiments of the invention may be arranged to administer UV-C light to fluid in a gaseous, liquid, or solid form or combination thereof at the point within the system wherein the temperature is the lowest. This may be advantageous as the motile behavior of microorganisms is affected by temperature. Motile bacteria show between a fivefold and sevenfold increase in average translational velocity as the environmental temperature is changed between 10° C. and 50° C. Within ice the microorganisms are effectively trapped and unable to move, this means that the UV-C light has a higher chance of irradiating the microorganism. The UV-C light is effectively reflected by the ice and this may be due to the ice having a micro-faceted surface or it may be due to the fact that a plurality of ice blocks (known as cubes when suitable for a drink) held in a reservoir have air gaps between the blocks so that light will reflect at the boundary of air and ice and only a proportion will propagate into the block. This means that given a suitable length of residence time the UV-C light will reflect sufficient times to irradiate the entire internal volume of the reservoir. This effect is even further magnified when the reservoir contains a mist (fog) or a foam as these both reflect light more efficiently then a body of water held in the same reservoir. This means that in some embodiments, the UV-C purification device is arranged at the point in the system wherein the temperature is the lowest. This may be, for example, the surface of the evaporator of an ice making machine, or the harvest bin of the ice making machine where the ice cubes are stored.

In other embodiments this may be the passageway between the ice cream mixing compartment and the dispensing nozzle of an ice cream machine.

Table 1 below shows experimental data of the concentration of microorganisms in molten ice per 0.1 ml.

TABLE 1

Ice test results

| | | 10 cups of 0.5 l ice dispensed | | | | | | | | | |
|---|---|---|---|---|---|---|---|---|---|---|---|
| | | 1 | 2 | 3 | 4 | 5 | 6 | 7 | 8 | 9 | 10 |
| Date | UVC | Concentration microorganisms in molten ice (per 0.1 ml) | | | | | | | | | |
| 22 Jul. 2015 | Off | 49 | — | — | — | — | — | — | — | — | 101 |
| 27 Jul. 2015 | Off | 41 | — | — | — | — | — | — | — | — | 54 |
| 24 Aug. 2015 | 4 mW | 0 | 0 | 0 | 0 | 0 | 0 | 0 | 0 | 0 | 1 |
| 25 Aug. 2015 | 4 mW | 0 | 1 | 0 | 2 | 0 | 0 | 0 | 2 | 1 | 0 |
| 14 Sep. 2015 | Off | 9 | 11 | 24 | 11 | 11 | 12 | 8 | 14 | 14 | 22 |
| 15 Sep. 2015 | Off | 17 | 175 | 16 | 19 | 13 | 32 | 18 | 26 | 27 | 52 |

It can be seen that over the 55 day test period that the number of microorganisms were significantly lower on the days where the UV-C light was administered to the ice.

Table 2 below shows the comparison between the number of microorganisms when no UV-C was administered to ice and when UV-C was administered to water and to ice.

TABLE 2

UVC test results
CFU/0.1 ml

| | H$_2$0-UVC | ICE - no UVC | ICE - UVC |
|---|---|---|---|
| Start conditions ("0") | 349 | 359 | 363 |
| After 1 hour ("1") | 4 | 186 | 3 |
| After 3 hours ("2") | 5 | 178 | 12 |
| After 6 hours ("3") | 10 | 170 | 10 |

It can be clearly seen from table 2 that the administering of UV-C light to water and to ice drastically reduces the number of microorganisms present in the test samples.

Embodiments of the invention further comprise a PCB upon which the UV-C LED chip is placed. The LED chip may contain an LED mount and a LED die. The LED mount may be a platform upon which the LED die is located. The PCB has a top surface and a bottom surface and the UV-C LED chip is mounted on the top surface. Additional electrical components, for example, sensors, capacitors, resistors may be located on the top surface with the UV-C LED chip or they may be located on the bottom surface of the PCB. This bottom surface location for the additional components may facilitate the location of more UVC LED chips on the top surface of the PCB, it may allow for a smaller PCB and hence a smaller module and/or improved cooling if the back of the PCB is exposed to air.

In some embodiments, modules may comprise multiple chips coupled to a single window element. The multiple chips might be arranged to form an array, for example, such that the window forms a single broad light emission surface. In other examples, however a single window element might be coupled to each individual chip. According to some embodiments, each module might comprise just a single LED-window assembly, while in others, modules might comprise arrangements of pluralities of LED-window assemblies.

In some embodiments, the one or more UV-C-transmissive window elements may have a top surface and a side surface and a hollow central portion to encapsulate the PCB, the side surface may further comprise a groove. The groove is there to allow the simple fitment of the module into the side wall of a reservoir containing a fluid in a gaseous, liquid, or solid form or a combination thereof. The hole in the reservoir is made slightly larger than the inner diameter of the groove but smaller than the outer diameter of the UV-C-transmissive window element. The upper and lower faces of the groove act as flanges that seal against the inner wall and outer wall of the reservoir containing the body of water or body of ice. This may prove advantageous as it allows the simple fitment of the module into the desired location without the use of any additional tools whilst still providing an adequate seal. In some embodiments, the one or more UV-C-transmissive window elements may be added as an overmolding. That is to say, the UV-C-transmissive window element may partially or fully encapsulate the PCB. The complete overmolding may prove advantageous as the resulting module may have increased robustness and/or water tightness compared with a partially overmolded module. The term encapsulate is broadly intended to mean the well-known LED encapsulation wherein liquid epoxy is poured over a LED die and sub mount in the LED molding chamber as well as partial or total encapsulation of the entire LED module or components thereof. Partial encapsulation may mean that all of the uppermost parts of the module are encapsulated wherein the lower parts are left free of encapsulation to enable fixation. The encapsulation may be permanent, removably affixed or indeed entirely removable and replaceable.

Since the LED module should be able to operate in humid conditions, and even under water, the UV-C transmissive element fulfills two important functions; firstly, it allows emission of UVC from the LED, and secondly, it provides a sealing functionality. This sealing may be a leak tight seal between the module and the fixing location, for example, the reservoir wall containing the space to be disinfected and/or the seal can be between the LED, PCB and the fluid to be purified.

In some embodiments, the PCB may be located in an additional housing, this housing may be any shape that proves advantageous. The PCB housing, for example, may surround the outer edge of the PCB. The PCB housing may be, for example, a shape that facilitates locating the module in the final location in which it will be used. In some embodiments, the PCB housing may comprise an externally threaded portion to allow a nut to be used to mechanically fix the UV module in position. In some embodiments, the PCB housing has a tapered pipe stub that is pressed into a suitably sized hole in the fixing location, for example, in the side wall of a reservoir. Due to the tapering of the stub portion, if the hole is correctly sized the fit between the stub and the hole starts as a clearance fit, passes through a transitional fit as more of the stub is passed through the hole and ends as an interference fit.

In some embodiments, the PCB housing has a straight stub, (i.e., it is not tapered) that is pressed into a suitably sized hole in the fixing location.

In some embodiments, the PCB housing has an annular flange that abuts the surface of the fixing location. The flange may be located at the end opposite to the PCB housing to it may be located at any position along the length of a stub portion. The flange may be designed to correspond to the surface features at the fixing location, this means that if the fixing location is a reservoir wall for example, and the reservoir wall is curved, the flange may be designed such that it corresponds to the curvature of the wall to allow a good seal.

In some embodiments, the flange is flat and in yet further embodiments a seal may be used between the flange and the fixing location to facilitate an adequate seal for the medium to be irradiated.

The flange may be glued, screwed, bolted, welded or any other known fixing means in position at the fixing location.

In some embodiments, the one or more UV-C transmissive window element may have a top surface, a side surface, a hollow central portion to encapsulate the PCB and PCB housing and a partial bottom region. The partial bottom region may be opposite the top surface of the UV-C transmissive window element, that is to say at the other end of the UV-C transmissive window element from the top surface. The partial bottom region may extend from the outer diameter of the UV-C module towards the center line of the PCB. By way of example, this can mean from the side surface of the UV-C transmissive window element towards the center line of the top surface.

In some embodiments, the partial bottom region has an inner surface and an outer surface. The inner surface may abut a feature of the PCB housing whilst the outer surface may be used to provide sealing in the final location. This PCB housing feature may be a groove, a flange, a flat region, an annular region, an undercut return or any other feature which would provide a region upon which the UV-C transmissive window element can seal, it may also be termed a sealing region.

In some embodiments, the UV-C transmissive window may be manufactured from silicone. The use of silicone may prove advantageous for sealing due to elastic, rubber-like properties (elongation of over 300%) and medium shore A hardness. A further advantage is that due to the conformability of the material it is possible to utilize molds with a negative draft angle. This means that features that normally cannot be included in a mold tool, such as an undercut, due to the molded material not being able to be released from the tool, can now be included. This simplifies the mold tool and brings cost benefits to the molding process.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
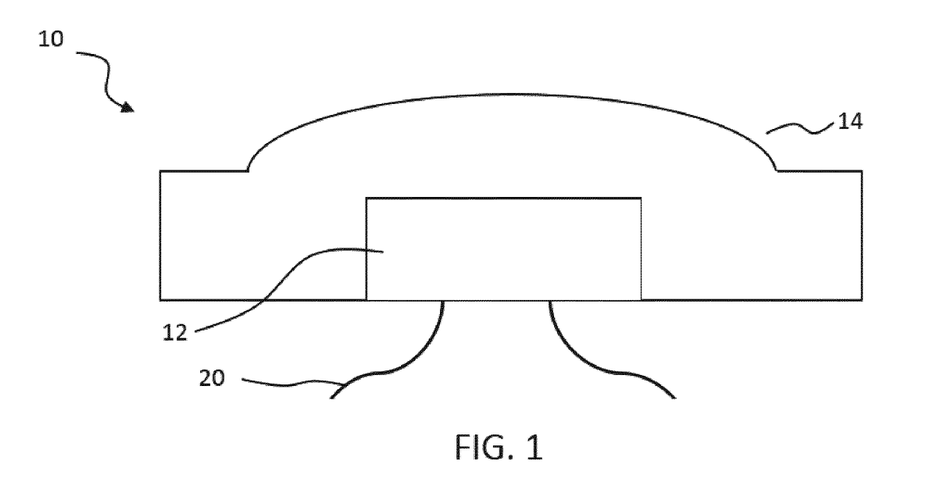
FIG. 1 shows a first example UV-C LED module, for administering of UV-C light to a fluid in a gaseous, liquid, or solid form or a combination thereof.

FIG. 1 shows a first example UV-C LED module 10 as comprised by embodiments of the invention. A UV-C LED chip 12 is in optical communication with a translucent window element 14, Wires 20 are provided for connecting the UV-C LED to a power source (not shown). This module may be placed in a location that is suitable to administer UV-C light to a fluid in a gaseous, liquid, or solid form or a combination thereof. Examples of the module 10 may be placed in a pipe, in a reservoir, a storage bin, a duct, a vessel, a shower head or a tap for example. The module may be integrated into a consumer device that is intended to be used within a consumer's home or it may be integrated into a professional device that is intended to be used in a business environment such as industry, restaurants, or fish markets for example. According to further examples, the UV-C LED module 10 may be partially or fully embedded within the structure of the device into which it is integrated, other examples may be simply placed on a suitable surface within the device.

Figure 2:
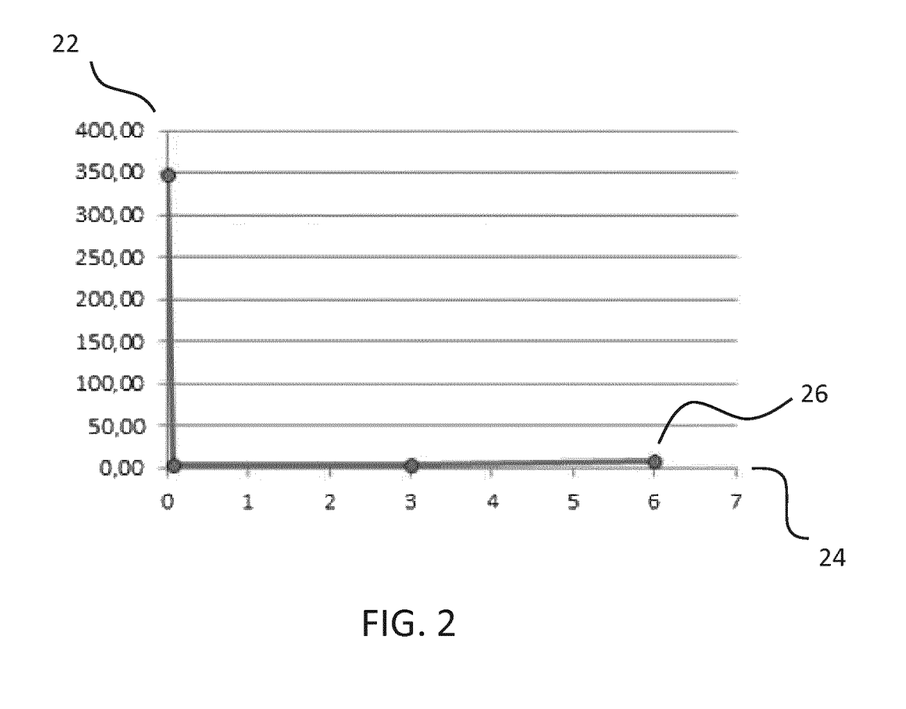
FIG. 2 shows a graph illustrating the number of microorganisms present in 0.1 ml of water after irradiation with UV-C light.

FIG. 2 shows a graph illustrating the number of microorganisms present in 0.1 ml of water after irradiation with UV-C light. The axis 22 represents the number of microorganisms, and the axis 24 represents the number of hours. Line 26 represents the number of microorganisms. As can be seen from the graph, the number of microorganisms was significantly reduced after the administration of a dose of 16 mJ/cm$^2$ UV-C. The dose in this example was applied in a single burst until the dose of 16 mJ/cm$^2$ was reached. The system was not sealed from the ambient environment.

Figure 3:
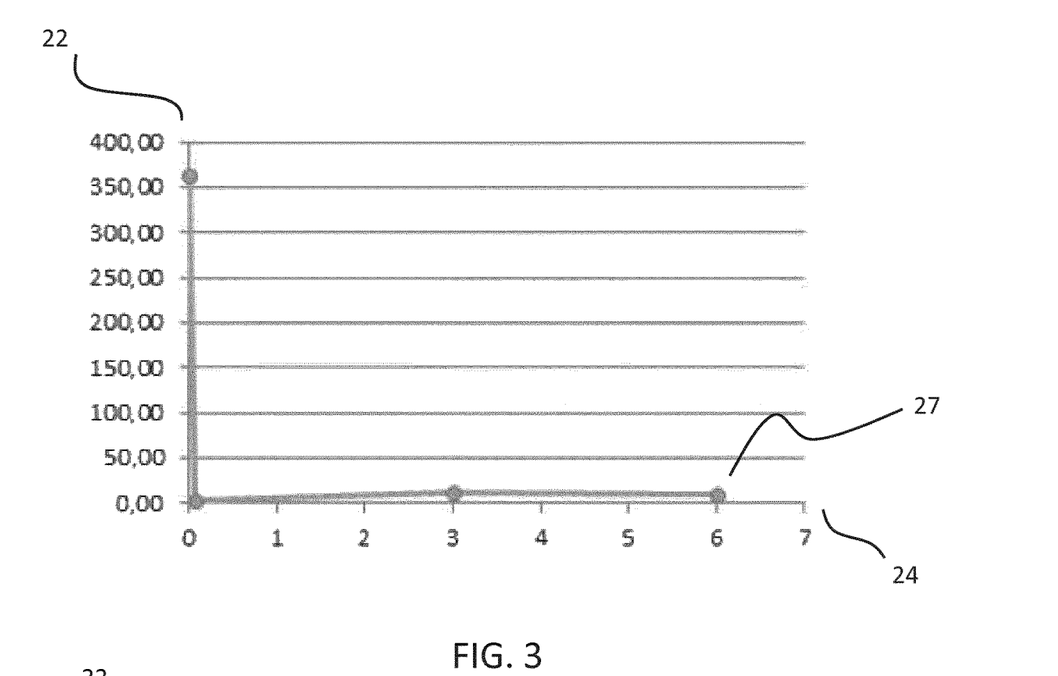
FIG. 3 shows a second graph, illustrating the number of microorganisms present in 0.1 ml of ice after irradiation with UV-C light.

FIG. 3 shows a graph illustrating the number of microorganisms present in 0.1 ml of ice after irradiation with UV-C light. The axis 22 represents the number of microorganisms, and the axis 24 represents the number of hours. Line 27 represents the number of microorganisms. As can be seen from the graph, the number of microorganisms was significantly reduced after the administration of a dose of 16 mJ/cm$^2$ UV-C, the initial sharp drop can be partially attributed to the freezing of the sample. The effect of temperature is one of the physical factors that affects growth and survival of microorganisms. Lowering the temperature below optimal values slows down or completely inhibits life processes of bacteria. The temperature determines the activity of bacteria, inter alia by changes in metabolism and modification of cellular structures (such as permeability of cell membranes). The temperature of a few degrees below 0° C. kills populations of many bacteria due to the mechanical damages of the cytoplasmic structures with the formation of ice crystals during the freezing of water. However, it is worth noting that very low temperatures affect the bacteria in another way. The bacteria can enter a state of suspended animation-anabiosis (maintaining their vitality). Sudden lowering of the temperature to below approximately −70° C. does not destroy the cellular components, the plasma structures are not affected. The dose in this example was applied in a single burst until the dose of 16 mJ/cm$^2$ was reached. The system was not sealed from the ambient environment.

Figure 4:
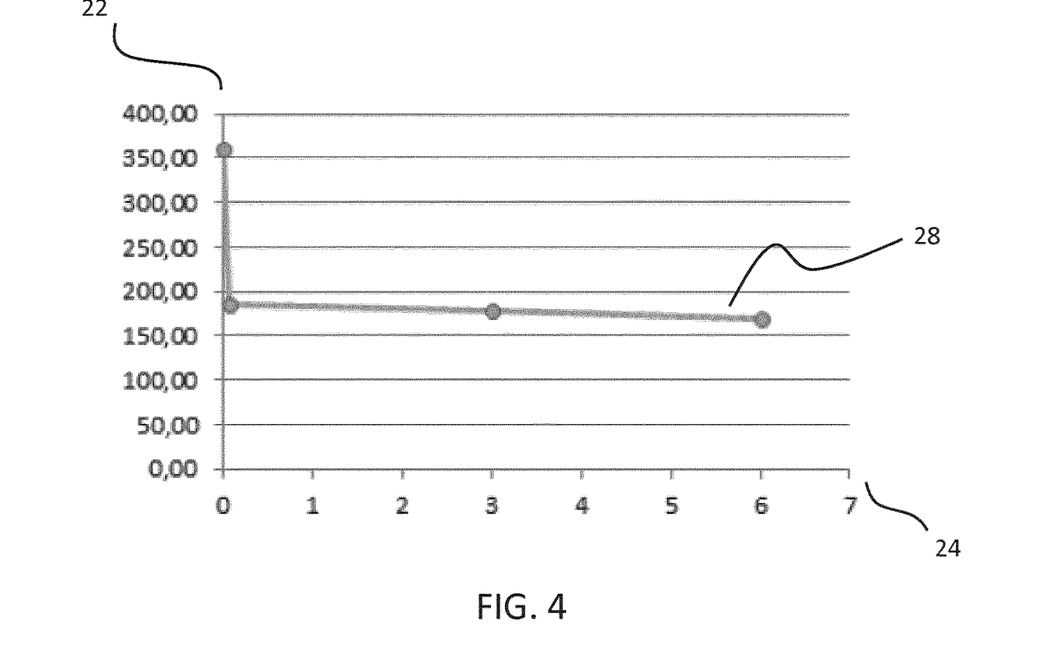
FIG. 4 shows a third graph, illustrating the number of microorganisms present in 0.1 ml of ice after no irradiation with UV-C light.

FIG. 4 shows a graph, illustrating the number of microorganisms present in 0.1 ml of ice after no irradiation with UV-C light. The axis 22 represents the number of microorganisms, and the axis 24 represents the number of hours. Line 28 represents the number of microorganisms. As can be seen from the graph, the number of microorganisms fell to approximately 50% of the initial number. The sharp drop at the start of the test can be attributed to the freezing of the sample. The system was not sealed from the ambient environment.

Figure 5:
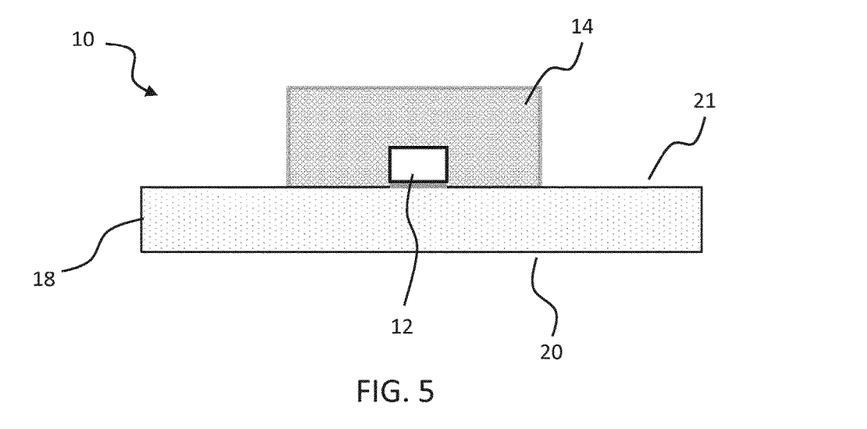
FIG. 5 shows a second example of a UV-C LED module for administering of UV-C light to a fluid in a gaseous, liquid, or solid form or a combination thereof.

FIG. 5 shows a second example of a UV-C LED module 10 for administering of UV-C light to a fluid in a gaseous, liquid, or solid form or a combination thereof. The UV-C chip 12 is placed on a PCB 18 and is in optical communication with a translucent window element 14. The PCB 18 has a bottom surface 20 and a top surface 21. In this example, additional electronic components are not shown but they may be placed on the top surface 21 or the bottom surface 20 of the PCB 18 whichever proves advantageous. It may be desirable to place the additional electronic components on the bottom surface 20 so that they are able to dissipate the heat generated within them to the ambient environment. The location of any additional electronic components on the bottom surface 20 of the PCB 18 may also allow for a smaller UV-C LED 10 as they can be located directly underneath the LED chip 12 and as such the size of the PCB 18 can be reduced.

Figure 6:
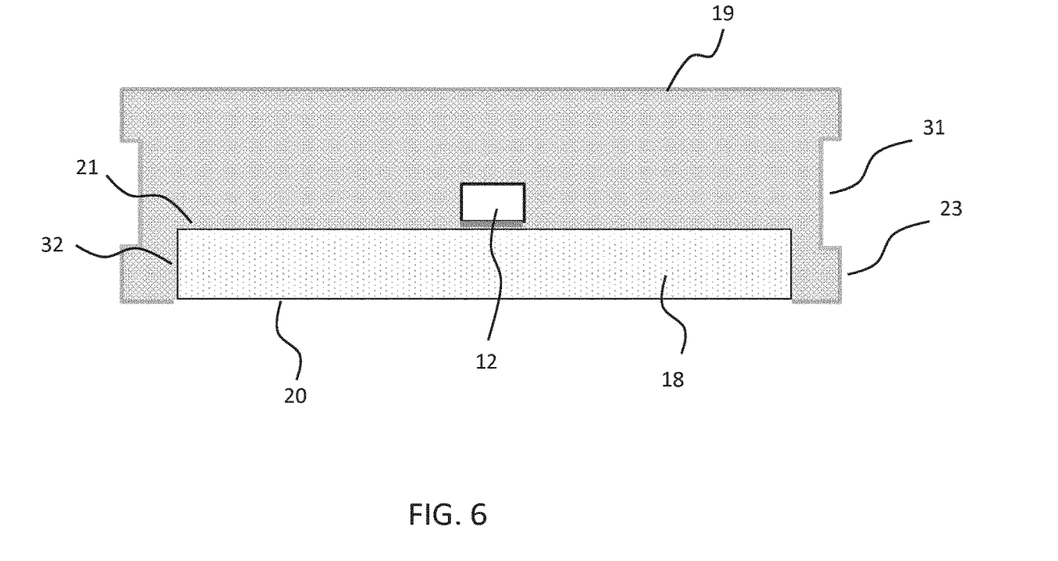
FIG. 6 shows a third example of a UV-C LED module for administering of UV-C light to a fluid in a gaseous, liquid, or solid form or a combination thereof.

FIG. 6 shows a third example of a UV-C LED module 10 for administering of UV-C light to a fluid in a gaseous, liquid, or solid form or a combination thereof. The UV-C chip 12 is placed on a PCB 18 and is in optical communication with a translucent window element 14. Furthermore, in this example, the translucent window element 14 surrounds and encapsulates the UV-C chip 12 and the upper surface 21 and side surfaces 32 of the PCB 18. This encapsulation may allow the UV-C module 10 to be placed in direct contact with the fluid. This encapsulation provided by the translucent window element 14 may also have design features such as a groove 31 provided in the side surface 23 of the UV-C module 10 to allow easy integration of the UV-C module 10 into a device. The fitment may be achieved without the use of any additional tools whilst still ensuring a good seal to prevent the leakage of the fluid. The translucent window element 14 may have a hollow central portion 25 (not shown) to act as a mixing chamber for the UV-C light emitted by the UV-C LED 12 in some examples or in others, the translucent window element 14 may be constructed to substantially conform to the UV-C LED die 12.

Figure 7:
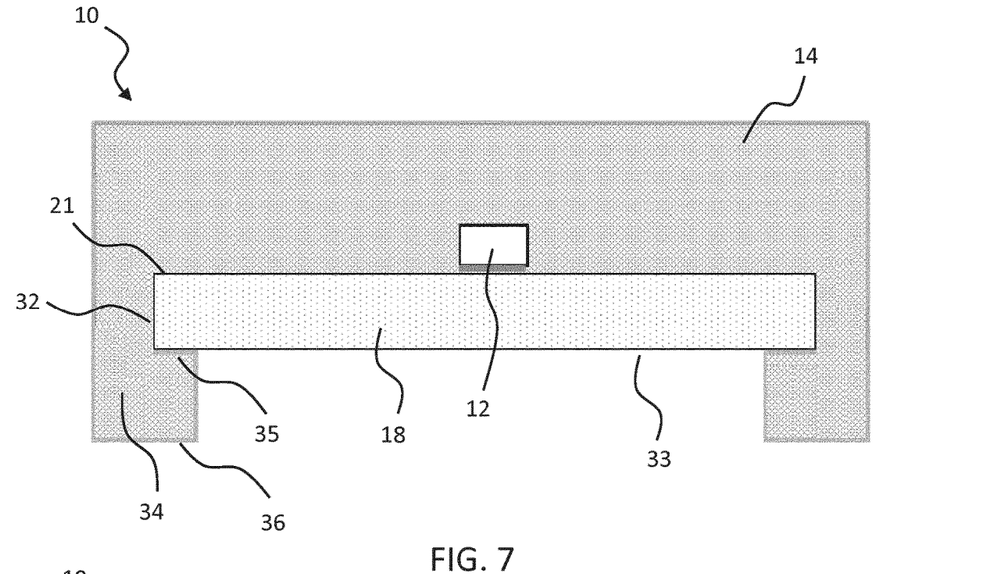
FIG. 7 shows a fourth example of a UV-C LED module for administering of UV-C light to a fluid in a gaseous, liquid, or solid form or a combination thereof.

FIG. 7 shows a fourth example of a UV-C LED module for administering of UV-C light to a fluid in a gaseous, liquid, or solid form or a combination thereof. The UV-C chip 12 is placed on a PCB 18 and is in optical communication with a translucent window element 14. Furthermore, in this example, the translucent window element 14 surrounds and encapsulates the UV-C chip 12, the upper surface 21, side surfaces 32 and bottom surface 33 of the PCB 18. This encapsulation may allow the UV-C module 10 to be placed in direct contact with the fluid. This encapsulation provided by the translucent window element 14 may also have design features such as a partial bottom region 34. This partial bottom region may have an inner surface 35 and an outer surface 36. The inner surface 35 provides a good seal against the bottom surface 33 of the PCB 18 and the outer surface 36 provides a good seal against the surface of the final location, for example, the wall of a reservoir (not shown) to allow easy integration of the UV-C module 10 into a device. The translucent window element 14 may have a hollow central portion 25 (not shown) to act as a mixing chamber for the UV-C light emitted by the UV-C LED chip 12 in some examples or in others, the translucent window element 14 may be constructed to substantially conform to the UV-C LED chip 12.

Figure 8:
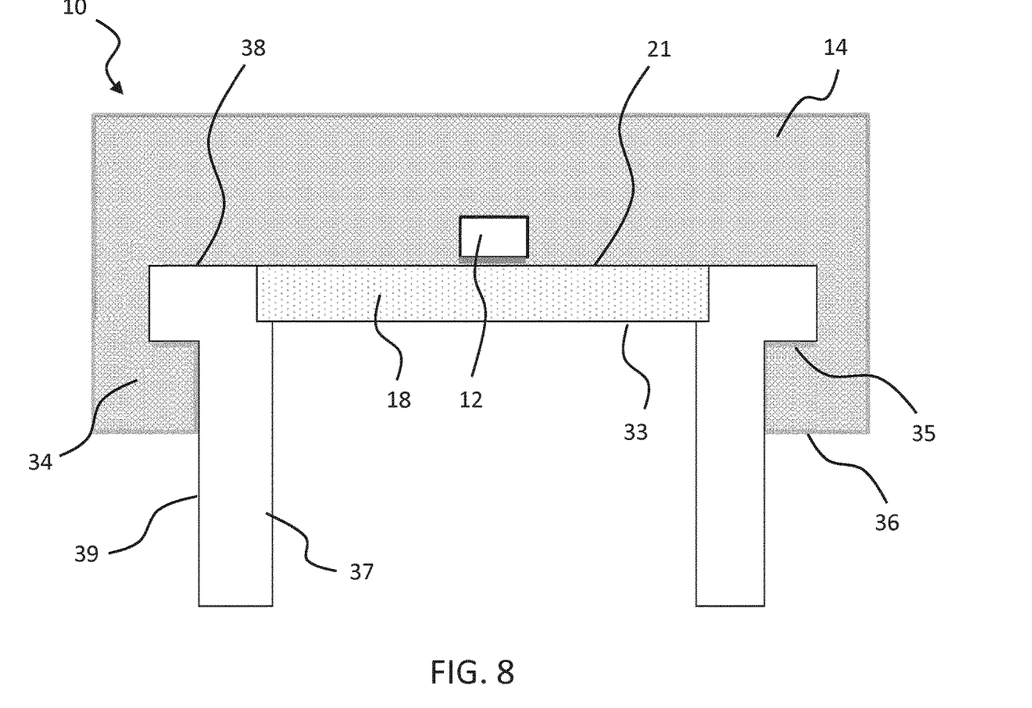
FIG. 8 shows a fifth example of a UV-C LED module for administering of UV-C light to a fluid in a gaseous, liquid, or solid form or a combination thereof.

FIG. 8 shows a fifth example of a UV-C LED module for administering of UV-C light to a fluid in a gaseous, liquid, or solid form or a combination thereof. The UV-C chip 12 is placed on a PCB 18 and is in optical communication with a UV-C transmissive window element 14. Furthermore, in this example, the UV-C transmissive window element 14 surrounds and encapsulates the UV-C chip 12, the upper surface 21 of the PCB 18, the upper surface 38, and at least a part of the side surface 39 of the PCB housing 37. This encapsulation may allow the UV-C module 10 to be placed in direct contact with the fluid. This encapsulation provided by the UV-C transmissive window element 14 may also have design features such as a partial bottom region 34. This partial bottom region may have an inner surface 35 and an outer surface 36. The inner surface 35 provides a good seal against a stepped surface 40 of the PCB housing 37 and the outer surface 36 provides a good seal against the surface of the final location, for example, the wall of a reservoir (not shown) to allow easy integration of the UV-C module 10 into a device. The UV-C transmissive window element 14 may have a hollow central portion 25 (not shown) to act as a mixing chamber for the UV-C light emitted by the UV-C LED 12 in some examples or in others, the translucent window element 14 may be constructed to substantially conform to the UV-C LED chip 12. In a preferred embodiment, the UVC transmissive window element 14 is made from silicone due to its conformable material properties.

In some embodiments, the UVC transmissive window element 14 may be removable and replaceable. This may be possible if the UVC transmissive element is manufactured separately to the rest of the module. It may be molded and then when the module is assembled the UVC transmissive window element may be fitted at least partially over the other elements.

In an exemplary example, the UVC transmissive element is molded using a silicone material. The UVC transmissive window element 14 has a top surface 19, side surfaces 23 and a hollow central portion 25. The LED chip 12 is mounted on the PCB 18 and the PCB is located within the PCB housing 36. The UVC transmissive window 14 is then fitted over the top of the LED chip, PCB and the upper portion of the PCB housing. Due to the previously discussed elasticity of the silicone, the UVC transmissive window element may be stretched over the PCB housing such that the LED chip 12 is located within the hollow central portion of the UVC transmissive window element. When the stretching force is removed from the UVC transmissive window element it will try to revert to its non-deformed state. This may increase the water tightness of the module as the UVC window element will almost be shrunk over the other components. Preferably, in some embodiments, the dimensions of the PCB housing will be slightly larger than the non-deformed dimensions of the UVC transmissive element 14. An advantage of the hollow central portion 25 may be that it allows the creation of an air space between the LED chip 12 and the underside of the UV-C transmissive window element 14, this air space may allow for light mixing or tailoring of the beam pattern for example. In other embodiments, the hollow central portion 25 is designed such that when fitted to the rest of the module it is in contact with the LED chip 12. In yet further embodiments, the hollow central portion 25 is designed such that it is conformable around the LED chip 12 when the module 10 is assembled.

Furthermore, the manufacture of the module may be cheaper if the separate elements can be manufactured in separate locations. A dedicated semiconductor factory may manufacture the LED chip 12, the chip may then be shipped to an assembly facility. The PCB 18 may be manufactured in a PCB manufacturing factory and the PCB housing and the UVC transmissive window element 14 may be molded at a molding factory. These components can then be shipped to the assembly facility for final assembly. The reason for the cost reduction lies in economy of scale and/or the location of the factories and facilities.

The PCB manufacturing facility may be making large amounts of PCBs and only a small fraction is cut to become the PCB 18 of the present module. Similarly, the molding factory may mold the PCB housing 36 and the UVC transmissive window element 14 in-between running other products on the same molding machinery.

In some embodiments, the top surface 19 of the UVC transmissive window element may further comprise beam shaping features. These may be in the form of lenses, dome shaped protrusions, surface features etc. The lenses may be collimating lenses, Fresnel lenses, diverging lenses or any combination thereof. The surface features may be prisms, domes, depressions, or any combination thereof.

The inventors have realized that materials such as silicone, Poly Crystalline Aluminium Oxide (PCA), UVC transparent glass, quartz, synthetic quartz (Si $O_2$), Fluorinated Ethylene Propylene (FEP) are suitable for the UV-C transmissive window element. A preferred material has elastic properties, can transmit UV-C wavelengths and is not susceptible to accelerated aging and degradation when exposed to UV-C wavelength radiation.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A UV-C purification device, comprising:
   one or more UV-C LED modules for administering UV-C light to a fluid in a gaseous, liquid, or solid form or a combination thereof, each module comprising:
   a printed circuit board (PCB), having a bottom surface and a top surface,
   one or more UV-C LED located on the PCB, and
   one or more UV-C-transmissive window elements,
   wherein the one or more UV-C LED is in optical communication with the one or more UV-C-transmissive window elements, and
   wherein the one or more UV-C transmissive window elements further comprises a top surface, a side surface and a hollow central portion to encapsulate the PCB and wherein the one or more UV-C transmissive window elements is removable and replaceable; and
   wherein the one or more UV-C-transmissive window elements surround and encapsulate the one or more UV-C LED and the top surface and side surfaces of the PCB.

2. A UV-C purification device according to claim 1 wherein the one or more UV-C transmissive window elements further comprises a partial bottom region opposite the top surface of the one or more UV-C transmissive window elements.

3. A UV-C purification device according to claim 1 wherein the partial bottom region of the one or more UV-C transmissive window elements may extend in a direction from the side surface of the UV-C transmissive window element, towards a centerline of the top surface of the UV-C transmissive window element.

4. A UV-C purification device according to claim 1 wherein the device further comprises a PCB housing surrounding the PCB.

5. A UV-C purification device according to claim 4 wherein the PCB housing surrounds the outer edge of the PCB.

6. A UV-C purification device according to claim 4 wherein the PCB housing further comprises a region upon which the one or more UV-C transmissive window element seals.

7. A UV-C purification device according to claim 4 wherein the PCB housing further comprises a fixation portion for fixing the UV-C LED module in a desired location.

8. A UV-C purification device according to claim 1 wherein the device further comprises a passage for the transportation or storage of the fluid.

9. A UV-C purification device according to claim 8, wherein one or more UV-C LED modules is arranged to illuminate a region of the passage.

10. A UV-C purification device according to claim 1, wherein the one or more UV-C-transmissive window elements (14) comprises a silicone material.

11. A UV-C purification device according to claim 1, wherein the UV-C purification device is any consumer device selected from the group of a fridge, a freezer, a coffee machine, an ice-cream machine, an ice making machine, a room humidifier, a cool drinks dispenser, a hot drinks dispenser, a slush drinks machine, an ice storage bin, a hot tub, an air conditioning device, a fire suppression device and a food processor.

12. A fluid purification method comprising, comprising:
 administering UV-C light to fluid in a gaseous, liquid, or solid form or a combination thereof, the UV-C light being generated by one or more UV-C LED modules, each module comprising:
  a printed circuit board (PCB) having a bottom surface and a top surface,
  one or more UV-C LED located on the PCB, and
  one or more UV-C-transmissive window elements,
 wherein the one or more UV-C LED is in optical communication with the one or more UV-C-transmissive window elements, and
  wherein the one or more UV-C transmissive window elements further comprises a top surface, a side surface and a hollow central portion to encapsulate the PCB; and wherein the one or more UV-C-transmissive window elements surround and encapsulate the one or more UV-C LED and the top surface and side surfaces of the PCB.

* * * * *